(12) United States Patent
Cook

(10) Patent No.: US 6,863,644 B1
(45) Date of Patent: Mar. 8, 2005

(54) BEVERAGE CONTAINER HOLDER

(75) Inventor: Matthew R. Cook, Chicago, IL (US)

(73) Assignee: LBP Manufacturing, Inc., Cicero, IL (US)

( * ) Notice: Subject to any disclaimer, the term of this patent is extended or adjusted under 35 U.S.C. 154(b) by 0 days.

(21) Appl. No.: 10/344,632

(22) PCT Filed: Aug. 24, 2001

(86) PCT No.: PCT/US01/26543

§ 371 (c)(1),
(2), (4) Date: Jun. 5, 2003

(87) PCT Pub. No.: WO03/018303

PCT Pub. Date: Mar. 6, 2003

(51) Int. Cl.⁷ .............................................. B31B 49/02
(52) U.S. Cl. ......................... 493/141; 493/69; 493/142; 493/151; 493/264; 493/409
(58) Field of Search ......................... 493/69, 141, 142, 493/150, 151, 183, 104, 259, 264, 291, 408, 409, 125, 108

(56) References Cited

U.S. PATENT DOCUMENTS

| | | | |
|---|---|---|---|
| 2,276,318 A | * | 3/1942 | Labombarde ................ 493/128 |
| 2,896,517 A | * | 7/1959 | Labombarde ................ 493/408 |
| 3,785,254 A | | 1/1974 | Mann |
| 4,056,046 A | | 11/1977 | Hughes |
| 4,144,800 A | | 3/1979 | Hughes |
| 4,201,332 A | | 5/1980 | Wooten |
| 4,285,680 A | | 8/1981 | Randles |
| 4,295,838 A | * | 10/1981 | Richards et al. ............ 493/105 |
| 4,418,865 A | | 12/1983 | Bowen |
| 4,605,464 A | | 8/1986 | Slevin |
| 4,614,512 A | * | 9/1986 | Capdeboscq ................ 493/441 |
| 4,624,653 A | * | 11/1986 | McBride et al. ............ 493/127 |
| 4,636,185 A | * | 1/1987 | Carter et al. ................ 493/127 |
| 4,708,708 A | * | 11/1987 | Fries, Jr. ..................... 493/357 |
| 4,892,223 A | | 1/1990 | DeMent |
| 4,897,982 A | | 2/1990 | Day et al. |
| 5,062,527 A | | 11/1991 | Westerman |
| 5,071,401 A | | 12/1991 | Bertsch |
| 5,090,616 A | | 2/1992 | Bertsch |
| 5,092,827 A | * | 3/1992 | McAdam et al. ........... 493/179 |
| 5,095,962 A | | 3/1992 | Lloyd-Davies et al. |
| 5,137,506 A | | 8/1992 | Haenel et al. |
| 5,158,371 A | | 10/1992 | Moravek |
| 5,205,473 A | * | 4/1993 | Coffin, Sr. .................. 229/403 |
| 5,238,632 A | | 8/1993 | Watters et al. |
| 5,671,861 A | | 9/1997 | Hall et al. |
| 5,749,493 A | | 5/1998 | Boone et al. |
| 5,803,346 A | | 9/1998 | Baker et al. |
| 5,941,421 A | | 8/1999 | Overman et al. |
| 5,993,877 A | | 11/1999 | Ohtake |
| 5,997,459 A | * | 12/1999 | Kruger et al. .............. 493/441 |

(List continued on next page.)

Primary Examiner—Rinaldi I Rada
Assistant Examiner—Sameh H. Tawfik
(74) Attorney, Agent, or Firm—Brinks Hofer Gilson & Lione

(57) ABSTRACT

A machine and method for producing beverage container holders of consistently high quality at high production rates and at an economical cost is disclosed herein. Beverage container holders (500) can be produced on the machine using the method disclosed herein at a rate of 50,000 beverage container holders per hour. The initial step of introducing the blanks 810) into the machine's conveying mechanism assures that the blanks are properly aligned and have a predetermined spacing there between, which avoids jamming of the machine and the resulting work stoppage (FIG. 2). The process includes steps for pre-breaking or pre-folding the flaps (FIG. 5) which enable the final folding of the flaps to be performed with the necessary reliability and speed. All except the final step of the manufacturing process are performed while the blanks are being conveyed at a constant high rate along the length of the machine.

46 Claims, 8 Drawing Sheets

U.S. PATENT DOCUMENTS

| | | |
|---|---|---|
| 6,102,252 A | 8/2000 | Overman et al. |
| 6,155,465 A | 12/2000 | Steiger |
| 6,170,715 B1 | 1/2001 | Evans |
| 6,186,361 B1 | 2/2001 | Teetsel, III |
| 6,227,440 B1 | 5/2001 | Hart |
| 6,244,592 B1 | 6/2001 | Baba et al. |
| 6,337,041 B1 | 1/2002 | Kuo |
| 6,421,984 B1 | 7/2002 | Murgatroyd et al. |
| 6,439,366 B1 | 8/2002 | Matkovich |
| 6,446,845 B1 | 9/2002 | Steiger |
| 6,474,040 B1 | 11/2002 | Ours et al. |

\* cited by examiner

BEVERAGE CONTAINER HOLDER

BACKGROUND OF THE INVENTION

A recyclable corrugated beverage container holder is disclosed in U.S. Pat. No. 5,205,473. The beverage container holder disclosed in this prior art patent if formed from a flat blank of material having a convex arcuate shape along a top edge portion and a concave arcuate shape along a bottom edge. The flat blank can be formed from a variety of corrugated materials, including corrugated cardboard. The material can have a single or multiple linerboards and the corrugations can be sinuous or angular. The side edges of the blank are generally radially extending from the center of the arcuate top and bottom edges. The flat blank is folded about a pair of folding axes to form a flat structure with overlapping edges that are secured to each other. The flattened structure can then be opened and has the shape of a frustum of a cone. Although this patent discloses steps for manufacturing this beverage container holder. It does not disclose a manufacturing process or method for producing the holders at high quality and at high volumes at an economical cost. Since this is a product that is intended to be used only once and then discarded along with the beverage container, the production cost must be minimized.

BRIEF SUMMARY OF THE INVENTION

The purpose of this invention is to produce beverage container holders at consistently high quality in large volumes at an economical cost. Beverage container holders can be produced on the machine using the method disclosed herein at a greatly increased rate. The beverage container holders produced with this machine and method are of high quality and are very useful products. The initial problem that was encountered in the development of this invention was the proper introduction of the blanks into the processing machine. It was found that, unless the blanks are initially properly aligned in the machine's conveying mechanism, the blanks would cause the machine to jam which would require stopping the machine, cleaning up the jam and restarting the manufacturing process. The machine and process disclosed herein have overcome that problem. To produce this product at this greatly increased rate, it was necessary to develop a process in which all of the operations of the process are performed while the blanks and the products in the manufacturing process are moving. The time necessary to decelerate and then reaccelerate in bringing the blank to a stop to perform a single operation would have made it impossible to achieve the improved rate. Another critical challenge that had to be overcome was that a heat-activated adhesive was to be applied to the inner surface of the beverage container holder which must be crystallized during the manufacturing process to prevent the inner surfaces of the product from adhering to each other. This was solved by applying streams of freezing air at precisely the right place and moment during the process.

Both flaps of the blank must be folded over during the manufacturing process. A procedure was developed that includes the steps of pre-breaking or pre-folding the flaps which enabled the final folding of the flaps to be performed with the necessary reliability and speed.

As a result of this invention, the beverage container holders disclosed herein can be reliably produced in a continuous machine process. In the process disclosed herein, an operator loads stacks of blanks at the beginning of the production line and a second operator picks up groups of the completed products that are in an imbricated formation and places the group in shipping cases.

DETAILED DESCRIPTION OF THE INVENTION

The blanks 10 used in the process and on the machine of this invention are produced by printing and die-cutting operations that are performed by a mechanism not included in this invention. Blanks of other designs and raw material substrates could be used in practicing the method of this invention and processed with the machine of this invention. However, the blanks disclosed herein and used in the preferred embodiment of this invention have a single linerboard and a single fluted corrugation. Although beverage container holders of other final designs could be produced using the method and machine disclosed herein, the final product disclosed herein has the fluted surface in contact with the beverage container and the linerboard side on the exterior. Indicia can be provided on the outer linerboard surface. As will be presently discussed, each blank will be folded along predetermined fold lines. Perforations are produced in the blank along these fold lines in the production of the blanks. Perforations are also produced during the production of the blanks in the area where the free ends of the blanks are secured together by adhesive. These perforations are formed in the linerboard surface to allow the adhesive to penetrate this surface.

In the following discussion of the method and machine 100 for producing beverage container holders from blanks 10 into a final product 500, directions, such as forward, left and right, are determined from a position in front of the machine 100 looking in the direction that the blanks advance during the processing steps. The machine 100 extends longitudinally over a considerable length and includes a number of work stations along its length. In the subsequent discussion, work stations along the left and right sides will be discussed. When discussing work stations on the left side of the machine 100, the direction of movement of the blanks 10 will be indicated by the direction of an arrow A and, when discussing work stations on the right side of the machine, the direction of movement of the blanks 10 will be indicated by the direction of an arrow B. In the preferred embodiment, there is an operator at the starting end of the machine who loads stacks of blanks into the machine 100 and a second operator at the finishing end of the machine who loads the finished product 500 into shipping cartons. In the preferred embodiment of the machine, the steps of converting blanks into the finished products are automatically performed by the machine as the blanks are conveyed by the machine 100 along its longitudinal length. The conveyors for conveying the blanks 10 along the length of the machine 100, as well as the mechanism for performing the processing steps on the blank, are all carried by or supported by the machine frame 102.

Figure 1:
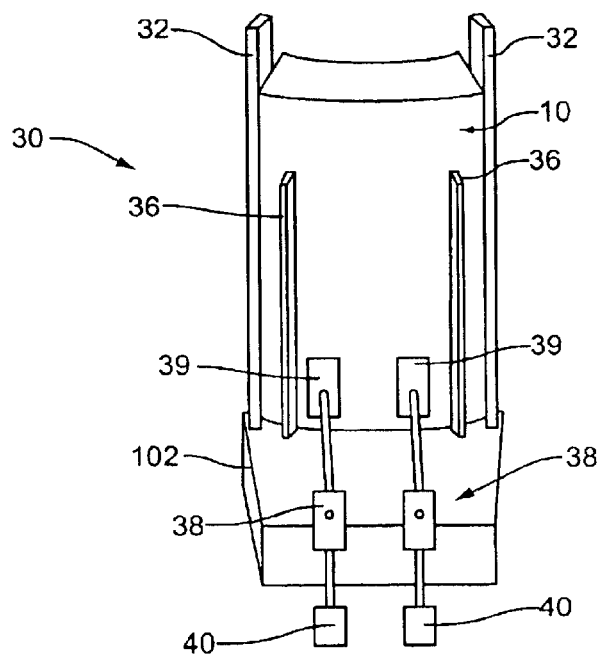
FIG. 1 is a front perspective view of the vertical containment apparatus.

There is a vertical containment apparatus 30, see FIG. 1, at the starting end of the machine that receives a stack of blanks 10. The blanks 10 are then sequentially released onto a set of introductory belts 50, see FIG. 2, that conveys them into the mouth 101 of the conveying mechanism of the machine 100. The speed of producing beverage container holders has been greatly increased as a result of the machine and method disclosed herein.

The vertical containment apparatus 30 includes side-bars 32, connected to the machine frame 102 that function to prevent the blanks 10 from moving to the left or right, and a pair of back braces 36 that function to hold the stack of blanks perpendicular to the mouth 101 of the machine 100 and prevent the stack from falling.

Figure 2:
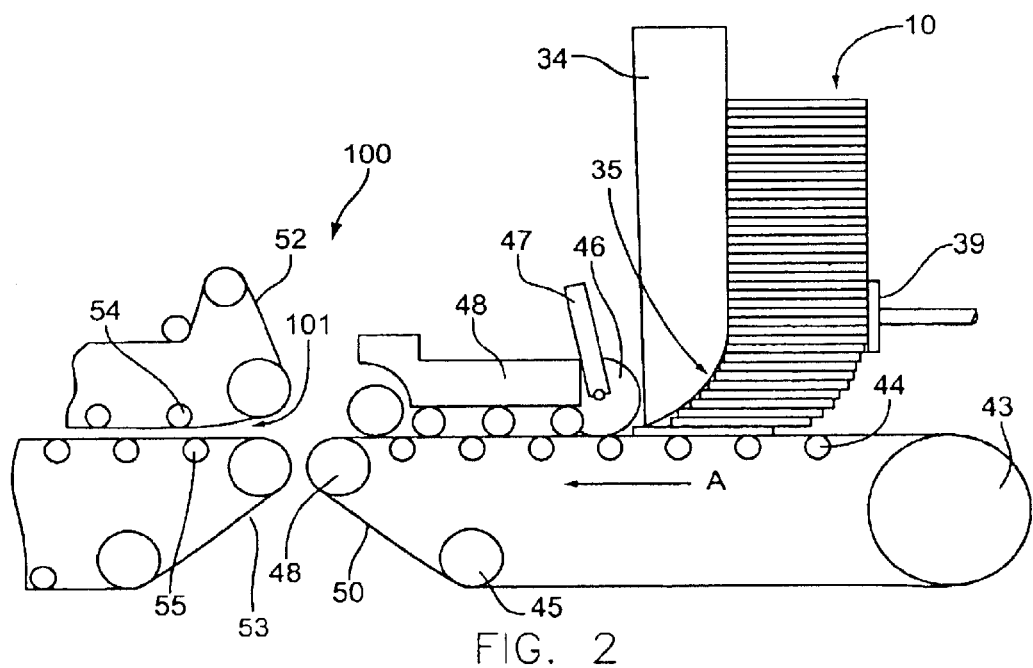
FIG. 2 is a schematic side view of the feed gate area of the machine.
Figure 3:
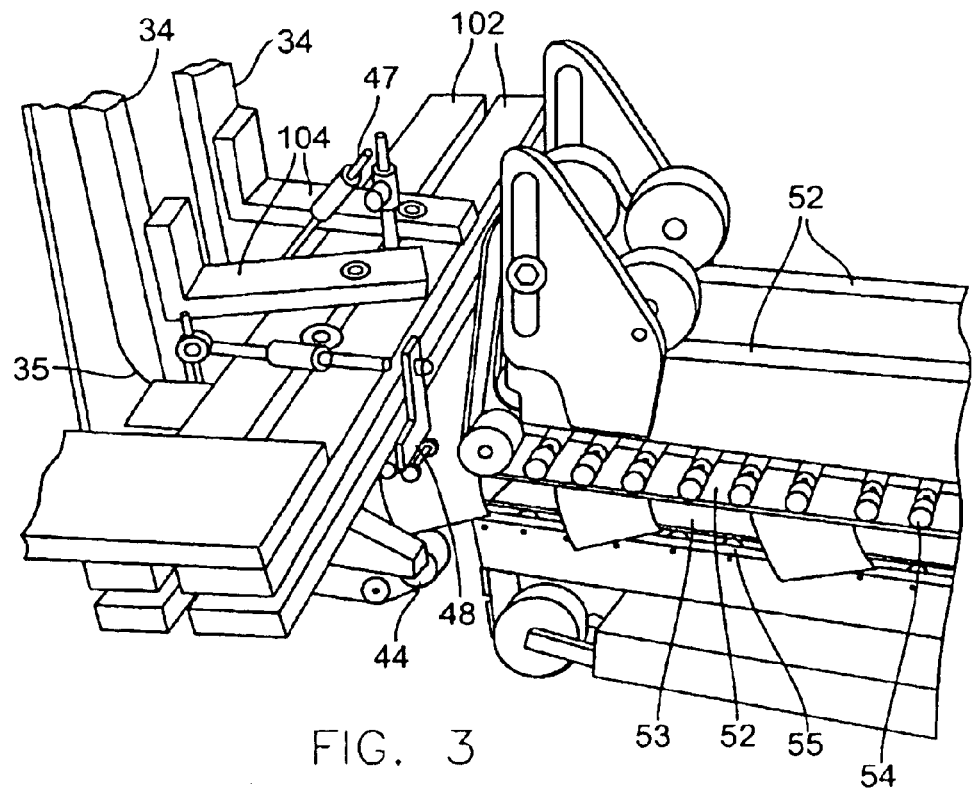
FIG. 3 is a perspective view of the feed gate and the mouth of the machine areas of the machine.

As best seen in FIGS. 2 and 3, the vertical containment apparatus 30 includes back brackets 34 having curved surfaces 35 along their bottom edges. Curved surfaces 35 function to guide the blanks 10 as they are sequentially conveyed forward from the bottom of the stack by the introductory belts 50. The back brackets 34 are supported by the machine frame 102, see FIG. 3, through L-shaped mounting bars 104. The back brackets 34 are connected to the L-shaped mounting bars 104 through a mechanism that allows the front brackets 34 to be finely adjusted in the vertical direction. This adjustment is to accommodate for the thickness of the blanks. When a shipment of blanks are received, they are generally of a uniform thickness. However, occasionally within a shipment of blanks as well as batches of blanks from a different manufacturer, there are blanks of a slightly different, general thickness. When this occurs, the back brackets 34 must be adjusted relative to the upper surface of the set of introductory belts 50 such that a single blank 10 can pass under the back brackets 34 when supported on the introductory belts 50.

The height of the vertical containment apparatus 30, as well as the supporting brackets 32, 34, 36, were custom designed to introduce blanks into the machine at the high rate that this machine has the capacity to produce finished products. The speed of the machine has dictated that the vertical containment apparatus has in excess of 200 blanks in it at all times. An operator is continuously adding blanks to the stack to insure that the vertical containment apparatus 30 always contains a minimum of 200 blanks. The brackets 32, 34, 36 also function to prevent the blanks from bending as they enter the mouth 101 of the machine 100.

The vertical containment apparatus 30 also includes a pair of vibrators 38 including flat pads 39 that bear against the back surface of the stack of blanks near the bottom of the stack. Horizontal vibratory motion is conveyed to the flat pads 39 from vibration producing mechanisms 40.

FIG. 2 is a schematic side view in which some structure, such as the side bar 32 and the machine frame 102, has not been shown to better illustrate the relationship between the back bracket 34 and the set of introductory belts 50 that function as a feed gate for the individual blanks 10. It should be noted that individual blanks 10 are fed from the bottom of the stack of blanks 10 held in the vertical containment apparatus 30. In FIG. 2, the left back bracket 34 is shown and it should be understood that an identical right back bracket 34 is hidden in this view by the left bracket 34. The front surface of the stack of blanks 10 is in engagement with the rear surface of the front brackets 34. The back brackets 34 have curved surfaces 35 at their lower ends. The vibrators 38 cause the blanks 10 at the bottom of the stack to move forward following the curved surfaces 35 of the back brackets 34. Below the stack of blanks 10 is a set of spaced introductory belts 50 that are driven, in the direction of arrow A in FIG. 2, by a drive drum 43. The set of drive belts 50 extend across the entire width of the blanks 10. There are a plurality of rollers 44 below the drive belts 42 and a take-up roller 45 for maintaining the belts taut. The bottom blank 10 in the stack rests on the upper surface of the set of drive belts 50 and is conveyed forward thereby. The back brackets 34 are adjusted relative to the upper surface of the set of drive belts such that there is a gap there between sufficient to permit one blank 10 to pass under the bottom tip of the back brackets 34. When a blank 10 emerges from under the back brackets 34, It encounters a central hold down roller 46 carried by a mounting rod 47 as well as banks of roller wheels 48 at the right and left ends of the blank 10. The central hold down roller 46 and the bank of roller wheels 48 are supported by the machine frame 102, see FIG. 3. In FIG. 2, the left bank of roller wheels 47 is visible which hides the right bank of roller wheels 47. The central hold down roller 46 and the right and left banks of roller wheels 47 exert a downward pressure on the top surface of the blanks 10, holding the blanks 10 into engagement with the set of introductory belts 50. This positive control of the blanks 10 as they are about to be fed into the mouth 101 of the machine 100 is critical to the proper operation of the machine 100. If a blank 10 is fed into the mouth 101 of the machine 100 in a crooked or twisted condition, the machine 100 will become jammed. This necessitates stopping the machine to remove the jam and involves down time which is highly undesirable.

The blanks 10 are placed in the vertical containment apparatus 30 with their fluted or corrugated side facing up and the concave arcuate bottom edge 11 being the leading edge as it enters the mouth 101 of the machine. The speed of the set of introductory belts 50 can be adjusted to thus control the rate that the feed gate introduces blanks into the mouth 101 of the machine. This allows the spacing between the blanks 10 as they proceed through the machine to be adjusted. In the preferred embodiment, a spacing of about ¾ of an inch is maintained.

After the blank is received in the mouth 101 of machine 100, it is continuously advanced through the machine 100 at a constant speed or rate until the completed product 500 reaches the final stage at which its forward speed is reduced and the finished product 500 assume an imbricated formation. In this imbricated formation, the trailing edge of each finished product overlies and is supported by the finished product 500 that is trailing it. Thus, the series of steps or processes that are performed on the blank to produce the finished product are performed while the blank 10 is moving at a constant speed. The blank 10 never stops its forward movement as it advances through machine 100.

The set of introductory belts 50 are relatively short and feed the blank into the mouth 110 of the machine which includes sets of upper 52 and lower 53 belts. Each set of belts 52 and 53 include two relatively narrow ribbon-shaped belts that are horizontally spaced from each other. The belts of the upper set 52 overlie the belts 53 of the lower set. As best seen in FIG. 3, the sets of belts 52 and 53 are narrower than the blanks 10 and, thus, the right and left ends of the blanks 50 extend in cantilevered fashion from the sets of belts 52 and 53. The sets of belts 52 and 53, as shown in FIG. 3, do not extend the entire length of the machine. Rather, a series of sets of upper and lower belts cooperate to convey the blanks along the length of the machine 100. However, throughout the length of the machine, all upper belts will be identified by reference number 52 and all lower belts will be identified by reference number 53. The upper surface of the lower rung of upper belt 52 is engaged by a series of freely rotating rollers 54 that function to exert a downward pressure on the blanks 10 and insure their constant movement along with belts 53. The lower surface of the upper rung of lower belt 53 is supported by a series of freely rotating rollers 55 that extend normal to the direction of travel of belt 53. The sets of belts 52 and 53 are narrower than the blanks 10 and the blanks 10 rest on lower belt 53 such that both ends extend in cantilever fashion from the longitudinal edges of the belts. This arrangement allows access to the free ends of the blanks by the various processing devices as the blanks advance along the length of the machine while the belts 53 and 54, as well as the subsequent sets of upper and lower belts, maintain positive control of the blanks 10. The speed of the belts 52 and 53 can be adjusted through the belt drive mechanisms.

Figure 4:
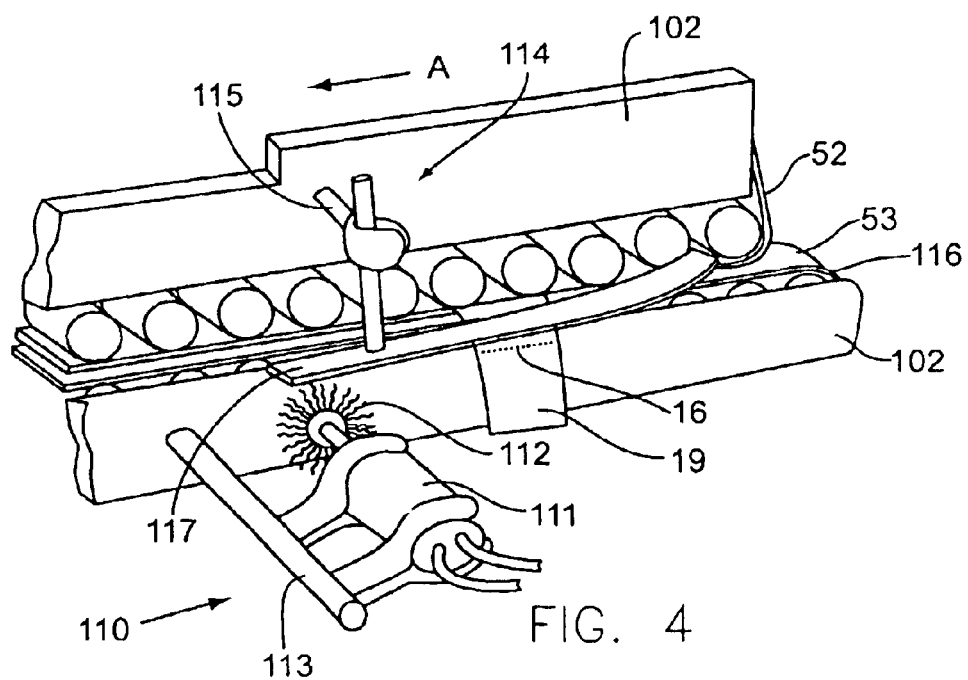
FIG. 4 is a perspective view of the skiving station.

The first processing station encountered by the blank 10 is the skiving station 110, which is shown in FIG. 4. This station is located on the left side of the machine 100 and the bottom surface of the left glue flap 19 is processed at this station. The blanks 10 are being carried between upper belt 52 and lower belt 53 in the direction of arrow A. The left glue flap 19 of a single blank 10 is shown in FIG. 4 extending outwardly in cantilever fashion from between belts 52 and 53. It should be noted that, when the machine 100 is operating, there would be a series of blanks 10 rather than a single blank as shown here for illustrative purposes. There is, at this station, a motor 111 that drives a rotating wire brush wheel 112. The motor 111 is supported by a motor mount 113 that extends from the machine frame 102. A guide and back-up member 114 is supported by a support 115 carried by the machine frame 102. The support 115 allows the guide and back-up member 114 to be vertically adjusted to accommodate for the thickness of the blanks 10. The guide and back-up member 114 is formed from an elongated strip of rigid sheet metal that has an upwardly curved guide section 116. The guide section 116 functions to guide the left glue flap 19 of the blanks 10 below the guide and back-up member 114. The guide and back-up member 114 also include a back-up section 117 that is located above the wire brush wheel 112. As the blanks 10 are conveyed through the skiving station 110, the wire brush engages the lower surface of the left glue flap 19 of the blank 100. The wire brush wheel 112 rotates about an axis that is normal to the direction that the blanks are advancing. The back-up section 117 of the guide and back-up member 114 is located above the wire brush wheel 112 as the blank is conveyed through this station 110. The top surface of the blank 10 is thus supported by the back-up section 117 when the wire brush wheel 112 is skiving the under surface of the glue flap 19. The skiving operation produces dust and a vacuum system can be employed in this area to maintain good working conditions for the machine operators as well as for the machine 100.

Figure 5:
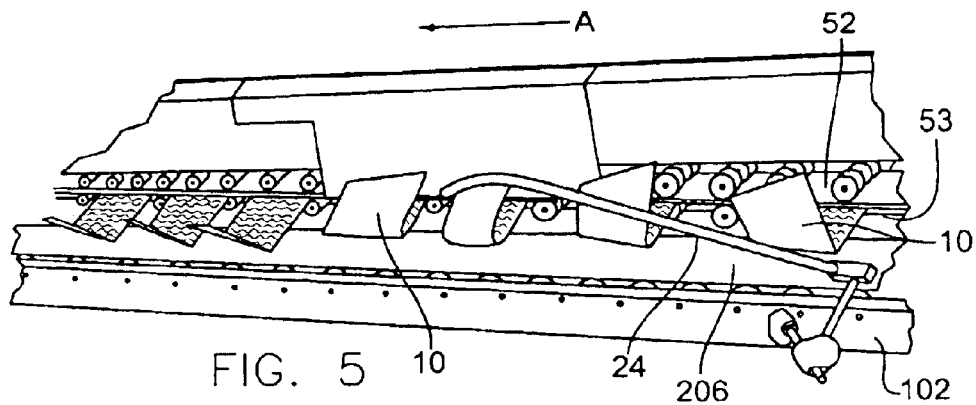
FIG. 5 is a perspective view of the mechanism for pre-breaking the left flap of the blank.

The blanks 10 continue moving from the skiving station 110, seen in FIG. 4, in the direction of arrow A, to the pre-brake station illustrated in FIG. 5. This station is located on the left side of the machine 100 and the left glue flap 19 is processed at this station. The left glue flap 19 is pre-folded along the perforated radial fold line 16 at this station. A brake bar 24, that is mounted on the machine frame 102, extends upwardly toward the machine and to the left, as seen in FIG. 5. The lower surface of the horizontally extending left glue flap 19 encounters the brake bar 24 and rides up on the bar causing the flap to bend or brake upwardly toward a vertical position along the perforated radial fold line 16 and then fold downwardly toward a folded over horizontal position. A belt 206 underlies the free ends of blanks 10 that are being transported between belts 52 and 53. After the folded left glue flap 19 moves past the brake bar 24, it is free to unfold back toward a horizontal attitude.

Figure 6:
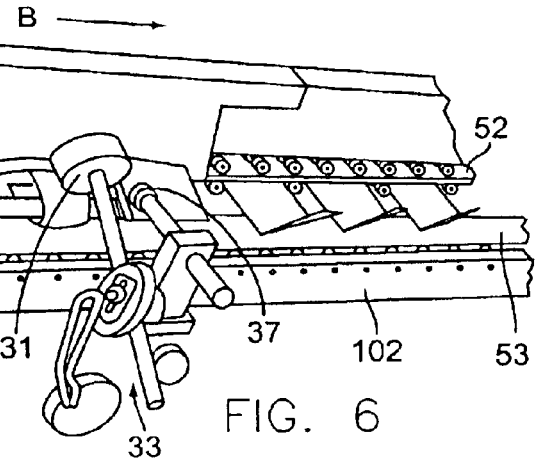
FIG. 6 is a perspective view of the mechanism for pre-breaking the right flap of the blank.

The pre-braking operation for the right overlap flap 20 is shown in FIG. 6. This operation occurs on the right side of the machine 100 and the blanks 10 are moving in the direction of the arrow B. The right overlap flap 20 is folded along the perforated radial fold line 17 at this station. A bend bar 27 that is mounted on the machine frame 102 extends horizontally along the upper surface of the blanks 10 over the central section 18 of the blanks 10. Bend bar 27 functions to maintain the central section 18 horizontal as the right overlap flap 20 is bent along perforated radial fold line 17. A first, relatively short brake bar 28, that is mounted on the machine frame 102, extends upwardly toward the machine and to the right, as seen in FIG. 6. The lower surface of the horizontally extending right overlap flap 20 encounters brake bar 28 and rides up on the bar causing the flap to bend or brake upwardly toward a vertical position along the perforated radial fold line 17. A second, longer brake bar 29 is then encountered by the right overlap flap 20 which causes the right overlap flap 20 to begin folding downwardly toward a folded over horizontal position. The folded down right overlap flap 20 then encounters a freely rotating press roller 31 that functions to continue pressing the flap 20 toward the horizontal position. The freely rotating press roller 31 is carried by a holder 33 that is supported on the machine frame 102. The folded over right overlap flap 20 then encounters a creasing member 37 that creases the fold along perforated radial fold line 17. After the folded right overlap flap 19 moves past the creasing member 37, it is free to unfold back toward a horizontal attitude.

Figure 7:
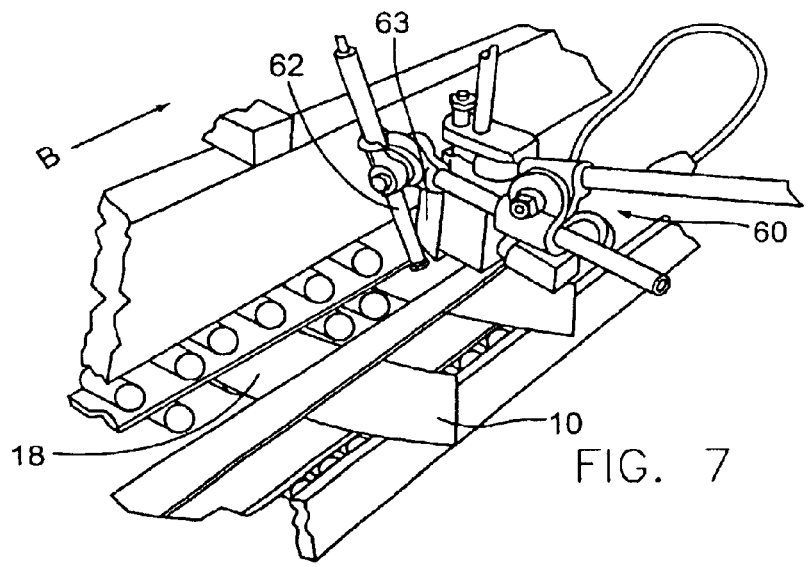
FIG. 7 is a perspective view of the work station at which the heat-activated adhesive is applied.

A station for applying the heat-activated adhesive 22 to the blank 10 is shown in FIG. 7. The view seen in FIG. 7 is on the right side of the machine and the blanks 10 are moving from left to right in this view. In this view of a station for applying the heat-activated adhesive 22, the heat-activated adhesive 22 is applied to the fluted or corrugated central section 18 of the blank 10. The mechanism seen in FIG. 7 is duplicated and, thus, not illustrated on the left side of the machine, and the heat-activated adhesive on the left side of the machine is applied to the fluted or corrugated side of the left glue flap 19. A holder mechanism 60, that is supported by the machine frame 102, is located above the blanks 10 at these stations. Electric eyes 62 are carried by the holder mechanisms. The electric eyes 62 sense the leading edge 11 of the blank 10 and sends a signal to the machines control mechanism which, in turn, sends a signal to a mechanism that causes the heat-activated adhesive 22 to be dispensed through the dispensing mechanisms 63 carried by the holders 60. As a result, two lines of heat-activated adhesive 22 are deposited on the fluted surface of the blank 10. This adhesive will soften in response to the hot beverage in the cup and cause the holder to adhere to the cup. This adhesive is at a temperature of about 295° F. when applied. The adhesive used for this purpose in the preferred embodiment of this invention is an industrial adhesive identified as 191-10 and from AABBIT Ade. of Chicago Ill.

Figure 8:
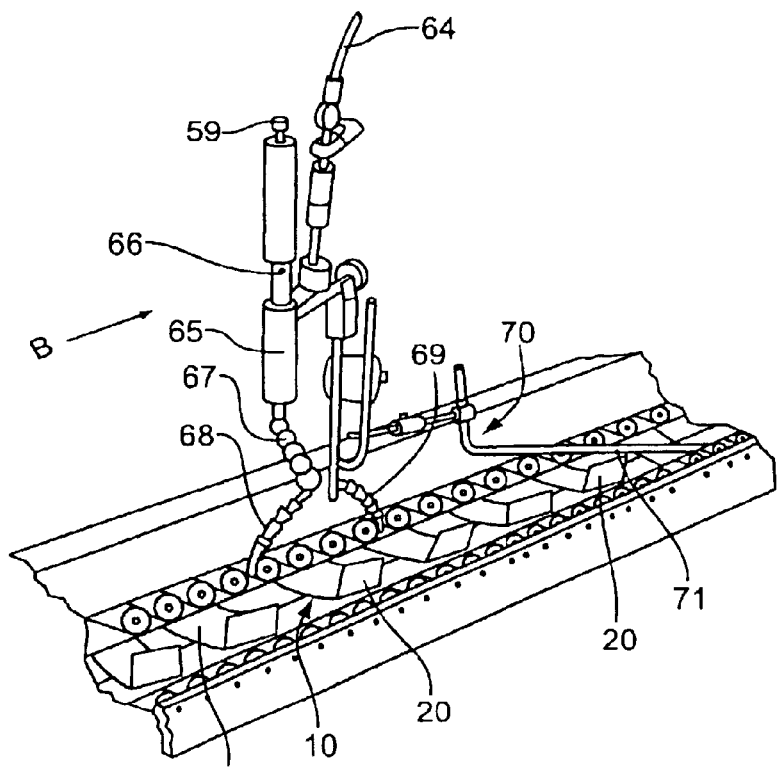
FIG. 8 is a perspective view of the work station at which cold air is applied to the heat-activated adhesive.

FIG. 8 shows the work station at which cold air is applied to the heat-activated adhesive 22 that has been deposited on the fluted surface of the central section 18 of the blank 10. The view seen in FIG. 8 is on the right side of the machine 100 and the blanks 10 are moving from left to right. In this view, the heat-activated adhesive 22 was applied to the fluted or corrugated central section 18 of the blank 10 and, thus, cold air is directed to this area of the blank 10. The mechanism seen in FIG. 8 is duplicated and, thus, not illustrated on the left side of the machine. The only difference in this device on the left side of the machine is that the heat-activated adhesive 22 that is being chilled was deposited on the left glue flap 19 rather than the central section 18. Pressurized air is received at these stations through tubes 64. The pressurized air is cooled and streams of freezing air, at a temperature of about 20° F., is directed on the heat-activated adhesive 22. This step crystallizes the heat-activated adhesive 22 sufficiently that it loses its ability to adhere or tack to the other side of the blank when the glue flap 19 and overlap flap 20 are folded over and pressed down in the area at which the heat-activated adhesive 22 was applied. In the preferred embodiment, ambient air that has been pressurized is fed through a vortex tube that converts a portion of the ambient air into a cold stream of air. In a vortex tube, the compressed air is throttled through nozzles that divide the air into hot and cold fractions that flow from opposite ends of the vortex tube. By controlling the relative dimension of the parts, the proportions of the hot and cold fractions can be adjusted. Reference can be made to U.S. Pat. No. 3,173,273 for a more complete disclosure of the method of operation of a vortex tube. The vortex tube is located in the cylindrical-shaped section 65 which is close to the point where the chilled air functions to crystallize the adhesive 22. An orifice of the vortex tube can be opened and dosed by a knob 59 which enables the temperature of the air being dispensed to be maintained at the desired temperature regardless of the surrounding air temperature. The hot air is exhausted through ports 66. Of course, a refrigeration unit could be used to supply freezing air for this cold air dispenser. The cooled air flows through a main branch 67 of a plastic air dispensing tube which then splits into first dispensing section 68 and second dispensing section 69, each of which terminates in a nozzle. The first dispensing section 68 discharges cold air on the heat-activated adhesive 22 which then receives a second blast of cold air from the second dispensing section 69.

As seen in FIG. 8, the right overlap flap 20 of the blanks 10 are folded up when they enter this work station. This is a result of the pre-braking of this flap that occurred at the work station illustrated in FIG. 6. As seen in FIG. 8, an L-shaped bar 70 is mounted on the machine frame 102 just past the location at which the cold air is dispensed. The generally horizontal leg 71 of the L-shaped bar 70 extends at an angle across the path of the upturned overlap flaps 20. As a result, the right overlap flaps 20 are returned to the horizontal attitude. This allow the blanks 10 to be received between another set of upper belts 52 and lower belts 53 which will take over the task of transporting the blanks along the length of the machine. This is necessary because, at the next work station, the left glue flap 19 will be folded flat against the central section 18 of the blank 10 and then seam adhesive 23 will be applied to the surface of the left glue flap 19 that was skived.

Figure 9:
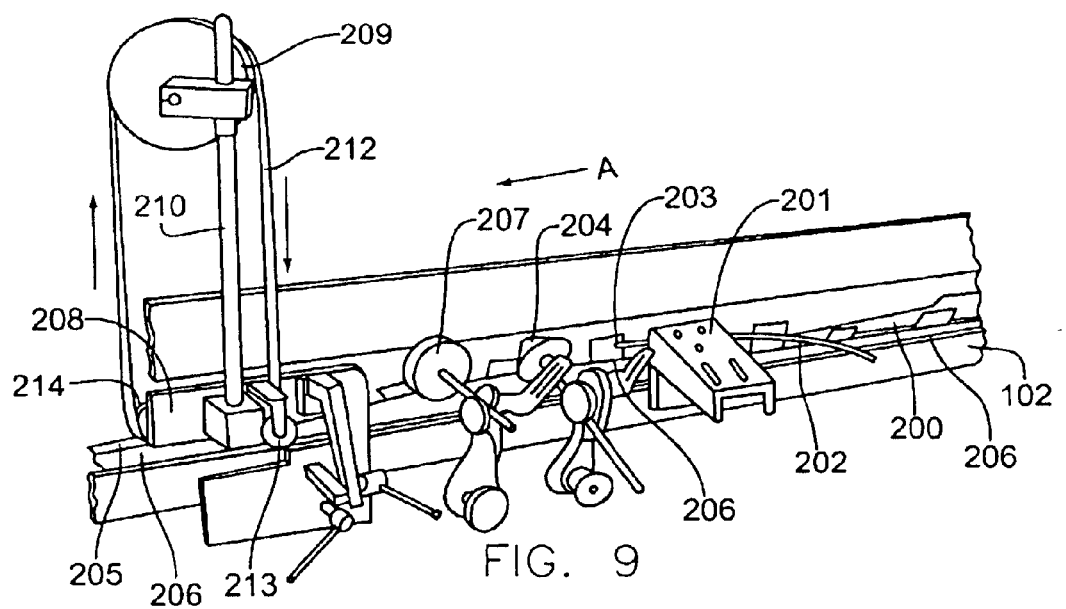
FIG. 9 is a perspective view of the work station at which the left glue flap is folded flat over the central section of the blank.

The next work station, illustrated in FIG. 9 of the machine 100, is where the left glue flap 19 is folded flat over the central section 18 of the blank 10. As seen in FIG. 9, the left glue flap 19 is moving from right to left. As the left glue flap 19 enters this work station, they are elevated a bit from the horizontal position. This is a result of the pre-braking of this flap that occurred at the work station illustrated in FIG. 5. A folding sword 200 is mounted on the machine frame 102 such that it overlies the blank 10 in the area of the perforated radial fold line 16. The folding sword 200 functions to hold down the central section 18 of the blank 10 and provide an edge along which the left glue flap 19 will be folded. A break bar 202, that is mounted to the machine frame 102, extends inward and over the tip of the folding sword 200 such that the leading edge of the folded up glue flap 19 encounters the break bar 202. The break bar 202 extends inwardly from the point where initial contact is made with the flap 19 to its free end 203. The leading edge and the bottom surface of the glue flap 19 slides along the break bar 202 causing the glue flap to pivot further toward the horizontal position. A carrier belt transition guide 201 is secured to the machine frame 102. The carrier belt transition guide 201 has three freely rotating, vertically orientated rollers through which the belt 206 is threaded. The location of belt 206 is also seen in the preceding work station that is illustrated in FIG. 5. Thus, belt 206 is twisted from a horizontal attitude to a vertical attitude. As a result, at the free end 203 of the break bar 202, belt 206 is vertically oriented and is functioning to orientate the glue flap 19 in a vertical orientation. The glue flap 19 continues to advance to the left, as seen in FIG. 9, to the position where the conical-shaped folding assist wheel 204 is located. The folding assist wheel 204 actually engages the upper or outer surface of belt 206 which, in turn, engages the glue flaps 19 as they move past this location. The conical-shaped folding assist wheel 204 causes the belt 206 to move from its vertical attitude to about a 45° angle and, in turn, causes the glue flap 19 to assume this attitude. The belt 206 next encounters the folding hold down wheel 207 that engages the upper surface of belt 206 causing it to move to a horizontal attitude. At this location, the glue flap 19 is folded flat over the central section 18 of the blank 10. During the above discussed process, illustrated in FIG. 9, the lower surface of the central section of the blank 10 has been supported by a bottom belt 205 which can be seen at the far left of FIG. 9. After the glue flap 19 leaves, the location of the folding hold down wheel 207, the flap is retained in the flat folded down attitude by a hold down mechanism 208 that sandwiches the flap 19 between belt 206 and the bottom belt 205. The hold down mechanism 208 provides positive control of the blank 10 after the left glue flap 19 has been folded flat on the central section 18 of blank 10. Hold down mechanism 208 includes a first roller 214, an upper sheave 209 and a second roller 213. Upper sheave 209 is mounted to freely rotate at the top of a mast 210. The belt 206 extends under roller 214, up and around sheave 209 and then down and around roller 213. The belt 206 is at this point horizontal and is moving from right to left as indicated by arrow A.

Figure 10:
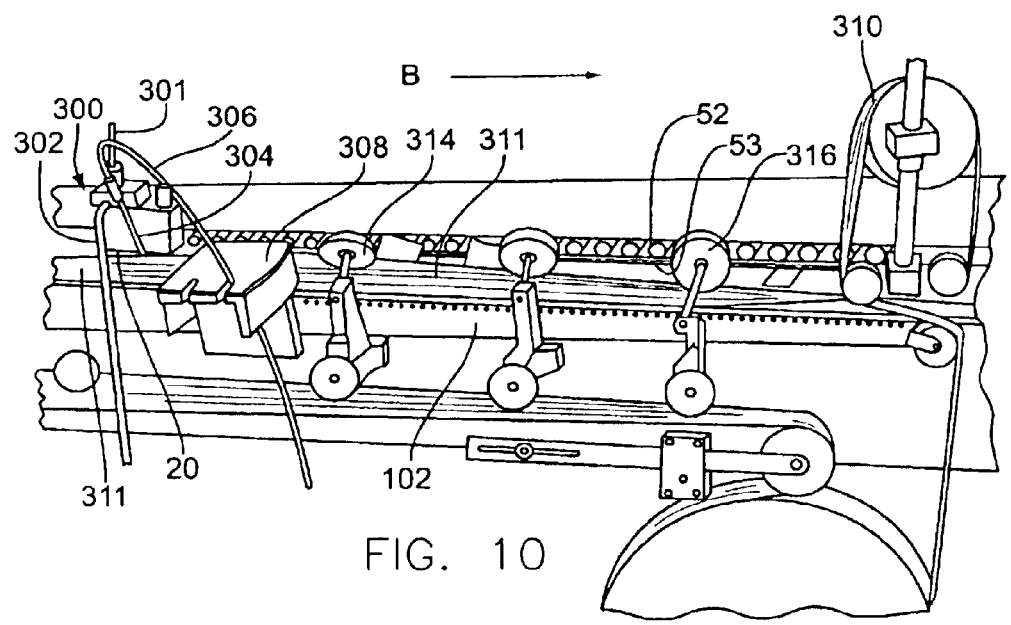
FIG. 10 is a perspective view of the work stations at which the hot melt seam adhesive is applied and the right overlap flap is folded over and pressed against the area where the adhesive has been applied.

In FIG. 10, the blanks 10 are being conveyed by an upper belt 52 and cooperating lower belt 53 from left to right. At this stage of the process, the skived area 21 of the left glue flap 19 that was produced on the linerboard which was the under surface of the blank at the skiving location is exposed on the top of the blank 10. The next step in the process is to apply the seam adhesive to the area that has been skived. The left glue flap 19 is held in the folded over attitude by the upper 52 and lower 53 belts with the area that was skived exposed to allow adhesive to be applied. As seen in the left most portion of FIG. 10, the hot melt seam adhesive 23 is being applied to the linerboard surface of the folded over left glue flap 19 that was skived. The hot melt dispenser 300 is supported on the machine frame 102 by a support bar 301. The hot melt dispenser 300 receives the hot melt adhesive through a flexible tube 302. An electric eye 304 senses the presence of a blank 10 and sends a signal to the machine processor through line 306 which, in turn, sends a signal back through line 306 to the dispenser 300 telling it when adhesive is to be dispensed. After the hot melt 23 has been deposited on the skived area of the left glue flap 19, the right overlap flap 20 is folded over and pressed down against the area where the adhesive 23 was applied. A carrier belt transition guide 308 is carried by the machine frame 102. The carrier belt transition guide 308 has three freely rotating vertically orientated rollers through which the upper course 311 of a belt 310 is threaded. The belt transition guide 308 functions to twist belt 310 from a horizontal orientation to a vertical orientation as it moves there through. The right overlap flap 20 was overlying the upper course 311 of horizontally orientated belt 310 as the blank 10 approached the area shown in FIG. 10. As the upper course 311 of belt 310 begins to transition, prior to entering the belt transition guide 308, from a horizontal orientation to a vertical orientation the right overlap flap 20 is pivoted upwardly about its perforated radial fold line 17. The upper course 311 is at a vertical orientation as to exits the belt transition guide 308 and has raised the right overlap flap 20 to the vertical attitude. As the blank 10 continues to move to the right, as seen in FIG. 10, it reaches a conical shaped folding assist wheel 314 that engages the outer vertical surface of belt 310 causing the belt 310 to move back toward the horizontal attitude and fold the right overlap flap 20 toward the horizontal folded position. As the blank 10 continues to move to the right, as seen in FIG. 10, the belt 310 encounters the folding hold down wheel 316 which is a puck-shaped wheel that presses the overlap flap 20 down into the folded over horizontal attitude over the skived area where the hot melt adhesive has been applied. At this point in the process, the blank 10 has been formed into the finished product 500 with the exception of a final step of continuing to press the right overlap flap 20 into contact with the left glue flap 19 for a sufficient time to allow the adhesive to set.

Figure 11:
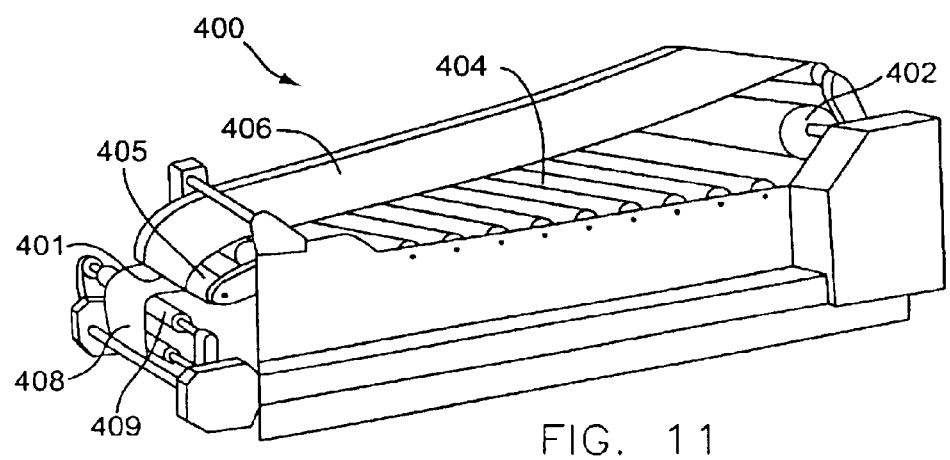
FIG. 11 is a perspective view of the pressure applicator.

As the product 500 continues to advance along the machine 100, it reaches the pressure application station of the machine 100. There is a pressure applicator apparatus 400, FIG. 11, at this station. The pressure applicator apparatus 400 includes an upper continuous belt 406 and a lower continuous belt 408 that forms a receiving mouth 401. The products 500 are fed by the upper belts 52 and lower belts 53 into the mouth 401 of the pressure applicator 400 and advance along the length of the pressure applicator 400. The upper belt 406 extends over a large drive drum 402 located near the end of the machine, and below a series of freely rotating rollers 404 that engage the internal surface of the lower rung of belt 406. The series of freely rotating rollers 404 includes an initial roller 405 that also engages the internal surface of the belt 406 along its forward edge. A lower belt 408 extends over an initial roller 409 that is followed by a series of adjustable rollers 409, all of which engage the underside of belt 408. An adjustment mechanism is provided for raising and lowering the series of rollers 409. By adjusting the lower belt 408 upward, the pressure exerted by the lower belt 408 on the finished product is increased. Thus, if, for example, when the operator performs a quality test on the product, he finds that the adhesive holding the two flaps together is not adequately securing the ends together, he can then adjust the location of the set of lower rollers.

Figure 12:
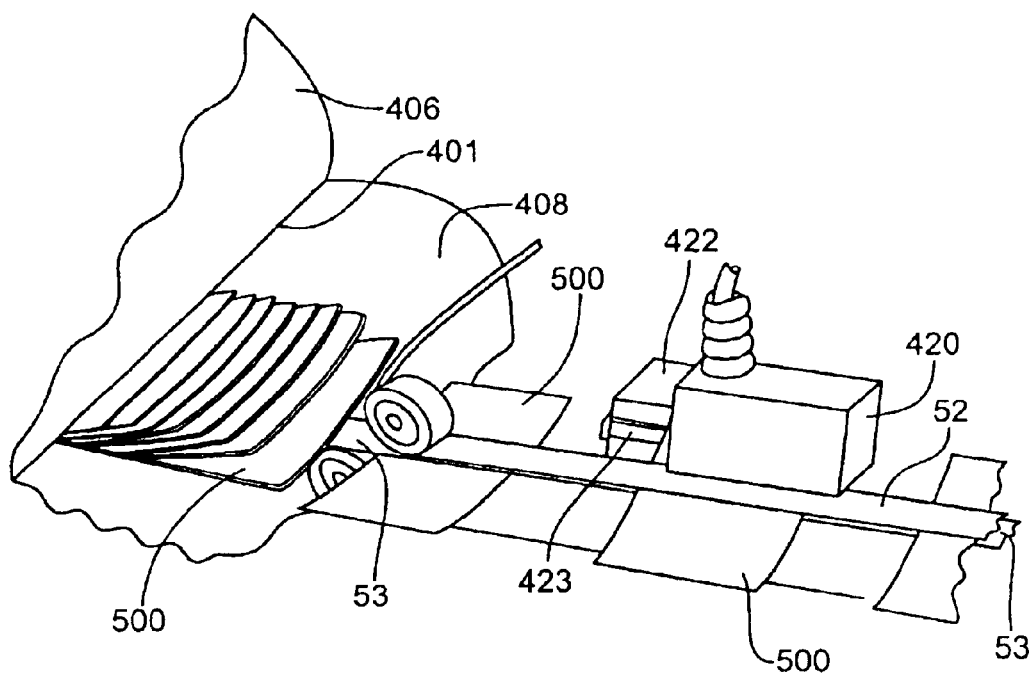
FIG. 12 is an enlarged perspective view of the finished product as it is being fed into the mouth of the pressure applicator.

FIG. 12 is an enlarged view of the products 500 being fed by an upper belt 52 and a lower belt 53 into the mouth 401 of the pressure applicator 400. It should be noted that belt 406 of the pressure applicator is driven at a slower speed than the belts 52, 53 and, thus, the spacing between the blanks 10 that existed when the product was being propelled by belts 52, 53 disappears once the products 500 enter the mouth 401 of the pressure applicator 400. The products thus enter and egress from the pressure applicator 400 in an imbricated formation with the leading edge of the product 500 supporting the product that precedes it. An electric eye 420 counts the products 500 as they feed into the mouth 401 of the pressure applicator 400, sending a signal to the machine's operating system as each product 500 is recognized. There is a kicker mechanism 422, having a kicker arm 423 pivoted thereto located slightly forward of the electric eye 420. The pivot axis of the kicker arm is such that, when it is pivoted, it will strike the last finished product that was counted by the electric eye 420 and displacing it from its usual orientation between belts 52 and 53. When the electric eye 420 has counted 134 products and sent these signals to the operating system, the operating system will send a signal to the kicker mechanism 422 causing the kicker arm 423 to pivot and displace a product 500 from its normal position in imbricated formation.

Figure 13:
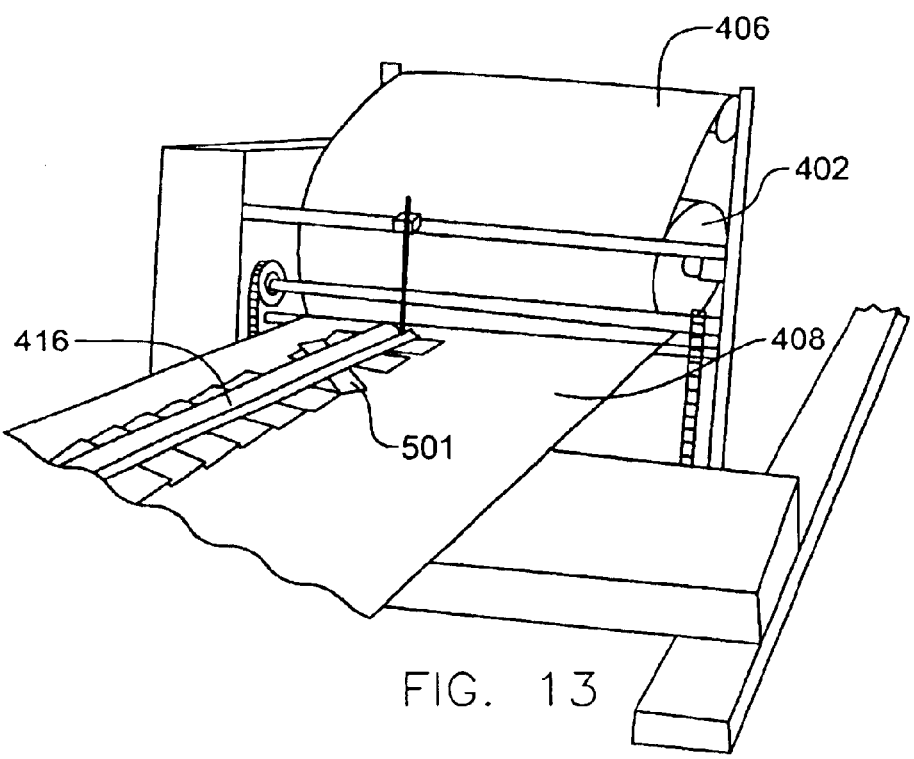
FIG. 13 is a perspective view from the back of the pressure applicator showing the finished product exiting the pressure applicator.

As seen in FIG. 13, when the finished products 500 exit the pressure applicator 400, they are in an imbricated formation with their leading front edge 11 under the trailing back edge of the preceding finished product 500. An elongated longitudinally extending metal bar 416 rests along the center of the line of finished products. Metal bar 416 is located at a point before the area where the finished products are picked up and placed in shipping cartons. A finished product 501 is shown in FIG. 13 that is not aligned with the other products 500. This is a product that was a 134th product and was kicked out of its normal position by the kicker arm 423. The number 134 is arbitrary and could be other numbers, for example, 100 or 150. The number 134 is used in the Applicant's preferred embodiment because 133 finished products fit in a row of the shipping carton into which they are packaged after exiting from the pressure applicator 400. An operator uses the kicked out finished product as a marker to pick up the next group of 134 finished products. Having the finished products arranged in an imbricated formation greatly facilitates picking up a row of 134 products by grasping the first and the 134th products, compressing them such that they assume a vertical attitude, and each finished product 500 lies flat against the adjacent finished products. With the finished products 500 having been compressed into a stack of finished products, the stack is then placed into a shipping carton.

The process for forming a beverage container holder from a blank 10 after it is fed out of the vertical containment apparatus 30 will now be discussed with reference to FIGS. 14–21. It should be noted that. In FIGS. 14–21, the blanks 10 are shown isolated from the machine 100 and its component parts are not shown in an effort to more clearly illustrate the beverage container holder manufacturing process. The blank, as fed from the vertical containment apparatus 30 and in the production process, as well as in the finished product form, are all seen in plan or top view in the FIGS. 14–21 series. Further, a single blank will start in FIG. 14 and progress step-by-step until the final manufacturing step shown in FIG. 11. Thus, the manufacturing process progresses step-by-step downwardly from the tops of the drawing sheets.

Figure 14:
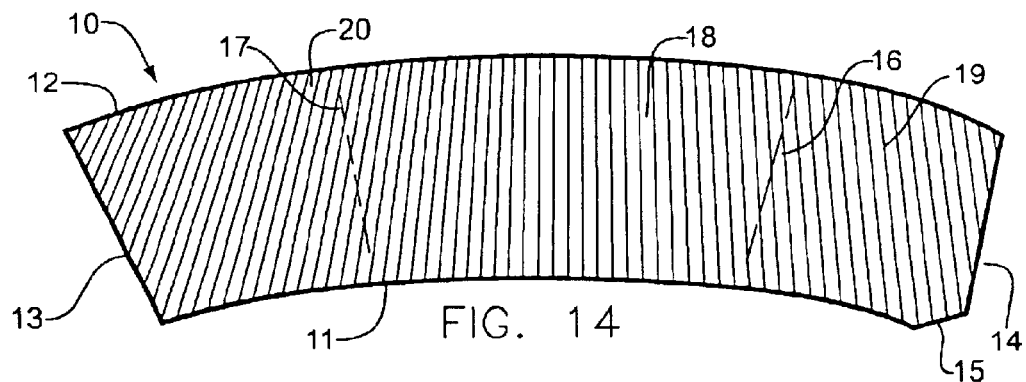
FIG. 14 is a plan view of an isolated blank as it starts through the processing machine with the corrugated or fluted side up.

As seen in FIG. 14, the blank 10 is shown as it would appear when supported on the introductory belt 50 after it has been kicked out of the vertical containment apparatus 30 with the linerboard side down and the corrugated or fluted side up. As seen In this series of Figures, the concave edge 11 of the blank 10 is the leading edge and the convex edge 12 is the trailing edge. The side edges 13 and 14 extend in a generally radial direction if the edges 11 and 12 are considered to be arch's of concentric circles. The corner at the intersection of concave edge 11 and side edge 14 has been trimmed off at 15 for a purpose to be discussed. Also seen in FIG. 14, two perforated radially folding lines 16 and 17 divide the blank 10 into a central section 18, a left glue flap 19 and a right overlap flap 20. As the blank 10 is fed through the machine 100, the blank 10 is supported on its central section 18, and the flaps 19 and 20 protrude outwardly therefrom in cantilevered fashion.

Figure 15:
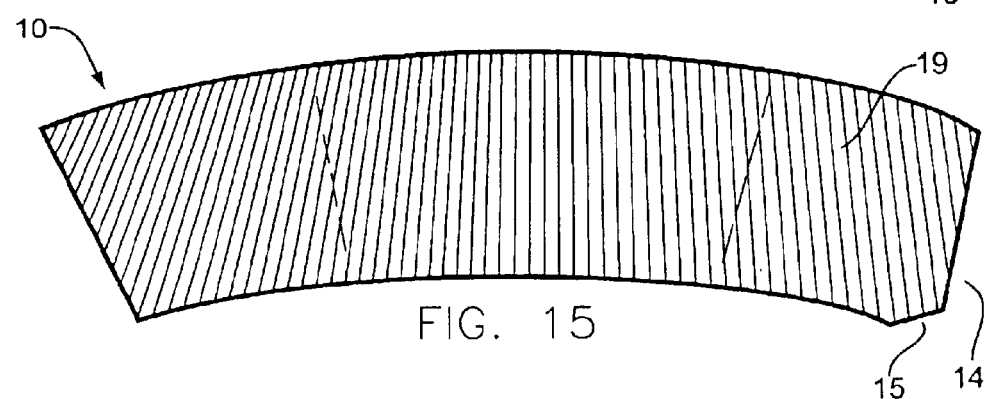
FIG. 15 is a plan view of an isolated blank as it is being skived.

In FIG. 15, the blank 10 is shown after being fed from the introductory belt 50 into the mouth 110 of the machine 100 and is at the skiving location 110. At this location, a skived area 21 is created on the linerboard surface of the glue flap 19, preferably along its free edge 14. Skiving is performed by a rotating wirebrush wheel 112 that is adjustably mounted such that the edge of the brush wheel 112 is in engagement with the undersurface of the glue flap 19. The wirebrush wheel 112 is mounted such that its peripheral edge engages the linerboard surface of the glue flap 19 which causes the wire tips of the brush wheel to come into contact with the smooth linerboard surface of the glue flap 19. Skiving serves two purposes, first it removes any corrugated dust and/or other particles created in the printing and die-cutting operations that are utilized to form the blanks 10. Second, the brush wheel removes the top layer of fibers from the outside of the blank. This important step causes inside fibers of the outside linerboard to stand up, thus rendering the surface more porous so that the seam adhesive can penetrate these inside fibers.

A pre-breaking or pre-folding operation is next performed on both free ends of each blank. In these operations, the left glue flap 19, as well as the right overlap flap 20, are folded up along the perforated radial fold lines 16 and 17, respectively. This pre-breaking or pre-folding operation functions to assure the proper operation of later steps in the process in which the flaps are completely folded over to a horizontal attitude.

Figure 16:
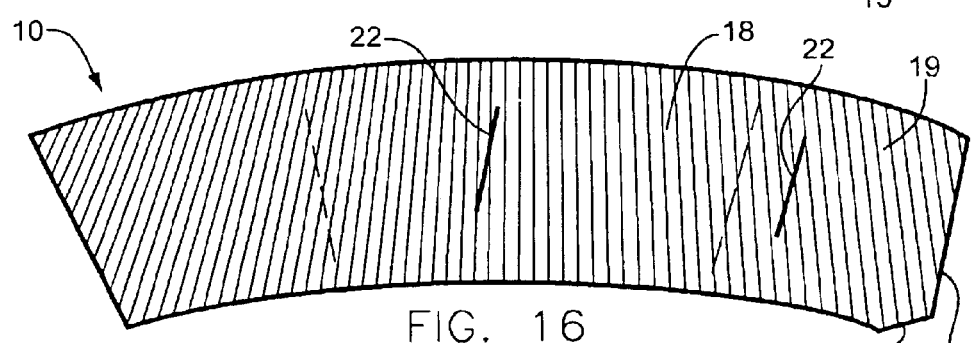
FIG. 16 is a plan view of an isolated blank as the heat adhesion glue is applied to is fluted surface.

The blank 10, as seen in FIG. 16, is at the location where heat-activated adhesive 22 is applied to the corrugated surface of the blank 10. Two beads of heat-activated adhesive 22 are applied to the surface that will become the inside surface of the beverage container holder. One of the beads 22 is applied to the central section 18 of the blank 10 and the other bead 22 is applied to the left glue flap 19. When a coffee purveyor fills a container with hot coffee, this heat-activated adhesive 22 will soften and function as an adhesive to prevent the beverage container holder from slipping down or off the container. The heat-activated adhesive is applied from a glue head that is pointing down from a holder mechanism 60 that is supported on the frame 102 of the machine 100, such that the adhesive beads 22 extend across a number of flutes at a slight angle extending from the leading edge 11 to the trailing edge 12. The two beads of adhesive 22 need not be applied simultaneously but both must be performed prior to the next step of chilling the adhesive.

One of the difficult problems that must be overcome in this manufacturing process is to prevent the heat-activated adhesive that has been applied to an inside portion of the beverage container holder from sticking to the other panel of the blank when the blank is folded over and then compressed. This phenomenon is called "blocking." If the heat-activated adhesive tacks the inside panels together, then the beverage container holder will not open and cannot be placed on a cup.

Figure 17:
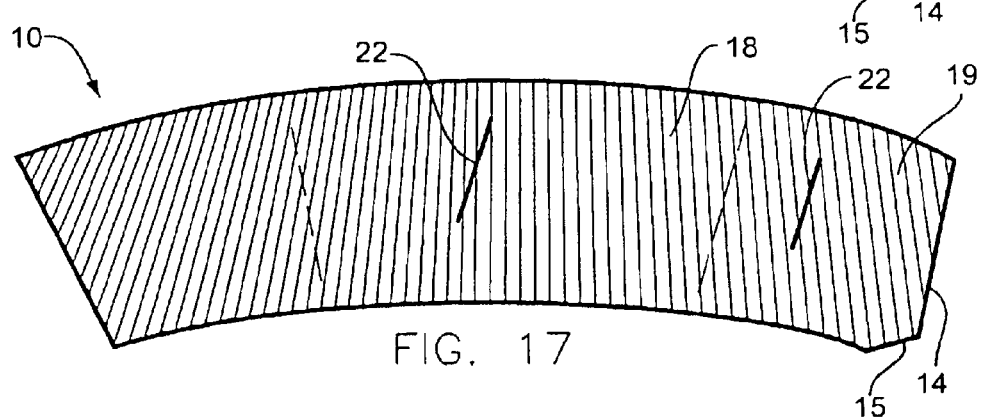
FIG. 17 is a plan view of an isolated blank as cold air is applied to the heat adhesion glue that was applied to is fluted surface.

After the heat-activated adhesive has been applied to the fluted surface of the blank 10, the blank proceeds to its location shown in FIG. 17. At this location, the machine frame 102 supports a cold air dispensing mechanism 63 for each of the beads of adhesive 22 that was applied to the blank. The cold air dispensing mechanisms 63 direct streams of freezing air on the beads of heat-activated adhesive 22. This step crystallizes the heat-activated adhesive sufficiently that it loses its ability to adhere or tack to the other side of the blank and, thus, prevents "blocking."

Figure 18:
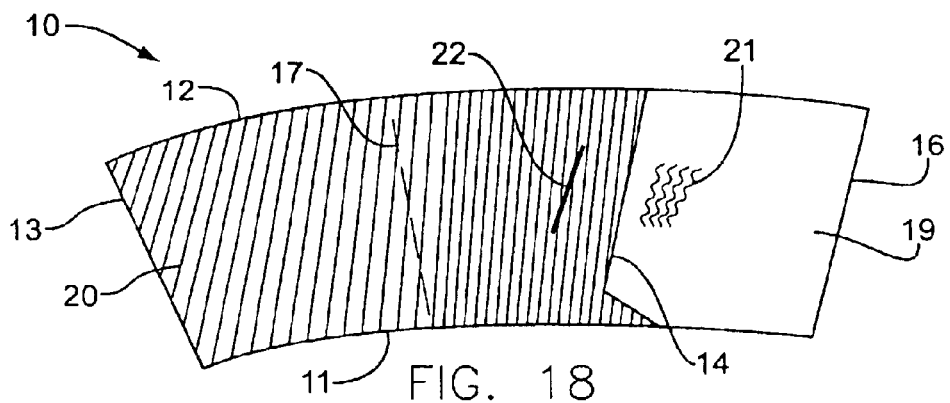
FIG. 18 is an isolated plan view of a blank after the glue flap has been folded along one of the folding axes.

After the heat-activated adhesive has been crystallized, the blank moves into the folding sections of the machine 100. As seen in FIG. 18, hold down mechanism 208 and its cooperating components have caused the left panel, called the glue flap 19, to fold over onto the fluted section of the blank 10. In the manufacturing process of the blank 10, prior to placing the stack of blanks into the vertical containment apparatus 30, a perforated radial fold line or score 16 was formed in the blank which defines this fold line of the blank 10. As seen in FIG. 18, the skived area 21 formed on the surface of the linerboard is visible.

Figure 19:
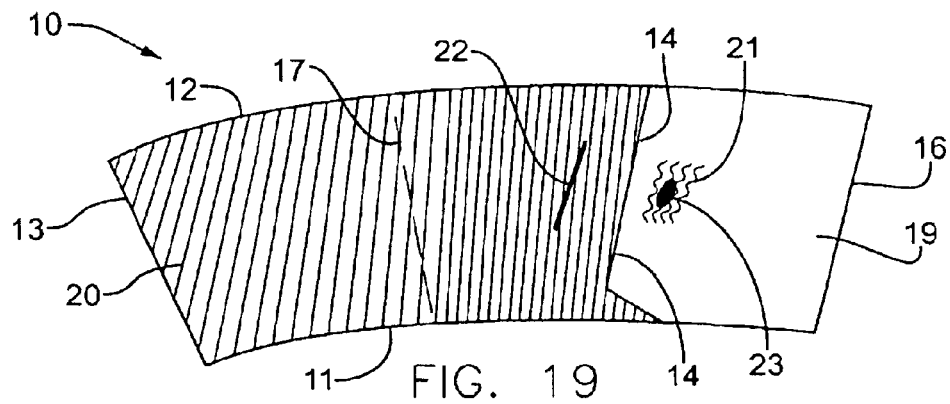
FIG. 19 is an isolated plan view of the blank after the left edge has been folded up along a folding axes and glue is being applied to the surface of the linerboard.

In FIG. 19, the seam adhesive 23 has been applied to the skived area 21 of linerboard surface. At this station of the machine 100, there is a hot melt dispenser 300 that dispenses hot melt or seam adhesive 23 to the skived area of the left glue flap 19.

Figure 20:
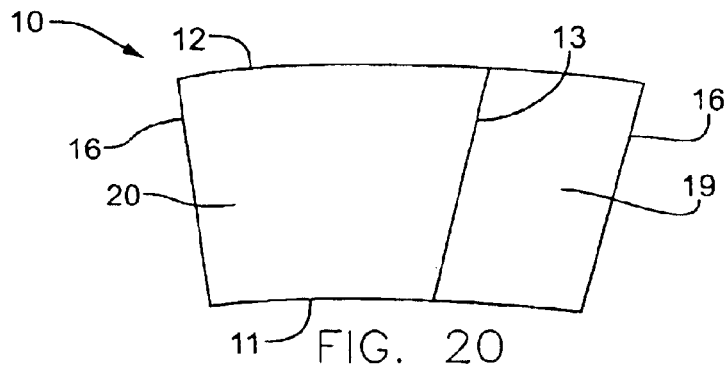
FIG. 20 is an isolated plan view of the blank after the right edge has been folded up along a folding axes such that it overlays the portion of the left edge upon which glue has been applied to the surface of the linerboard.

In FIG. 20, folding hold down wheel 316 and its cooperating components have guided the right panel, called the overlap flap 20, such that it has been folded along the perforated radial fold line 17 such that its free end overlies the skived area 21 of the glue flap 19 where the seam adhesive 23 was deposited.

Figure 21:
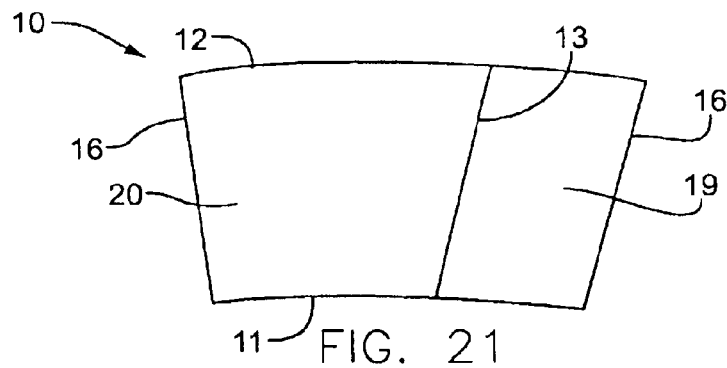
FIG. 21 is an isolated plan view of the blank while pressure is being applied to secure the overlapped portions of the right and left edges together.

In FIG. 21, pressure is being applied by the pressure applicator 400 to the overlapped area of the overlap flap 20 and glue flap 19 which results in securing the free ends of the blanks 10 to each other. At this location of the machine 100, there is pressure applicator 400 in the form of a belt 406 that is driven by a large driven drum 402 and extends over a freely rotating roller bar. Pressure is applied at this station and the product is now completed and ready to be packaged for shipment.

The process for producing the finished product has now been completed. Since the finished product is flat, it can be conveniently packaged in containers and shipped to the locations of the beverage purveyors. When the final products are opened they have the shape of frustum of a cone that coincides with the conical frustum of the beverage containers.

What is claimed is:

1. A method of manufacturing beverage container holders comprising the steps of:
   providing a stack of elongated blanks, each blank having a central section and two end flaps, said blanks being of a uniform thickness and having an outer and an inner surface;
   providing a conveyor mechanism that engages the central section of said blanks and conveys the blanks at a constant rate from the beginning of the process through we a last folding step of the process;
   releasing blanks from the stack, sequentially in an orientation with the outer surface down and the inner surface up, into said conveyor mechanism;
   skiving the outer surface of an end flap of each released blank;
   folding each of the end flaps up about a fold line and releasing them to return toward their unfolded positions;
   folding up the end flap that has been skived such that it lies flat over the central section of the blank;
   applying adhesive to the skived area of the flap that is laying flat over the central section of the blank;
   folding up the other end flap of the blank such that it overlies the skived area to which adhesive has been applied;
   providing a pressure applicator mechanism that conveys the folded blank at a rate that is slower than said constant rate and applies a downward pressure to the folded blank; and
   feeding the folded blanks to said pressure applicator mechanism that applies pressure to the free end flap that overlies the skived area to which adhesive has been applied and discharges the finished products.

2. A method of manufacturing beverage container holders as set forth in claim 1 comprising the additional step of:
   providing a containment apparatus for receiving the stack of elongated blanks;
   providing said containment apparatus with side bars and a back brace to assure proper alignment of the blanks when they are released into the conveyor mechanism.

3. A method of manufacturing beverage container holders as set forth in claim 1 comprising the additional step of:
   providing a containment apparatus for receiving the provided stack of elongated blanks; and
   providing said containment apparatus with front brackets, side bars and a back brace to assure proper alignment of the blanks when they are released into the conveyor mechanism.

4. A method of manufacturing beverage container holders as set forth in claim 1 comprising the additional step of:
   providing a containment apparatus for receiving the provided stacks of elongated blanks; and
   providing a set of introductory belts that underlies said containment apparatus and provides a support surface for said stack of elongated blanks.

5. A method of manufacturing beverage container holders as set forth in claim 4 comprising the additional step of:
   providing said containment apparatus with side bars and a back brace to assure proper alignment of the blanks when they are released into the conveyor mechanism.

6. A method of manufacturing beverage container holders as set forth in claim 4 comprising the additional step of:
   providing said containment apparatus with front brackets, side bars and a back brace to assure proper alignment of the blanks when they are released into the conveyor mechanism.

7. A method of manufacturing beverage container holders as set forth in claim 6 comprising the additional step of:
   supporting said front brackets such that there is space between the bottoms of the front brackets and said support surface equal to said uniform thickness to allow single blanks to be conveyed past said front brackets by said introductory belts.

8. A method of manufacturing beverage container holders as set forth in claim 7 comprising the additional step of:
   providing said front brackets with curved surfaces against which the leading edges of the blanks of said stack of elongated blanks engage as they approach said space between the bottoms of the front brackets and said support surface.

9. A method of manufacturing beverage container holders as set forth in claim 7 comprising the additional step of:
   providing vibration producing mechanism including pads that engage the trailing edges of the blanks of said stack of elongated blanks to assist in releasing the blanks from the stack.

10. A method of manufacturing beverage container holders as set forth in claim 1 comprising the additional steps of:
    applying heat-activated adhesive to an area of the inner surface of each blank; and crystallizing the heat-activated adhesive that has been applied to the area of the inner surface of each blank.

11. A method of manufacturing beverage container holders as set forth in claim 10 comprising the additional step of:
    providing a containment apparatus for receiving the provided stack of elongated blanks; and
    providing said containment apparatus with side bars and a back brace to assure proper alignment of the blanks when they are released into the conveyor mechanism.

12. A method of manufacturing beverage container holders as set forth in claim 10 comprising the additional step of:
    providing a containment apparatus for receiving the provided stack of elongated blanks;
    providing said containment apparatus with front brackets, side bars and a back brace to assure proper alignment of the blanks when they are released into the conveyor mechanism.

13. A method of manufacturing beverage container holders as set forth in claim 10 comprising the additional step of:

providing a containment apparatus for receiving the provided stacks of elongated blanks; and providing a set of introductory belts that underlies said containment apparatus and provides a support surface for said stack of elongated blanks.

14. A method of manufacturing beverage container holders as set forth in claim 13 comprising the additional step of:

providing said containment apparatus with side bars and a back brace to assure proper alignment of the blanks when they are released into the conveyor mechanism.

15. A method of manufacturing beverage container holders as set forth in claim 13 comprising the additional step of:

providing said containment apparatus with front brackets, side bars and a back brace to assure proper alignment of the blanks when they are released into the conveyor mechanism.

16. A method of manufacturing beverage container holders as set forth in claim 15 comprising the additional step of:

supporting said front brackets such that there is space between the bottoms of the front brackets and said support surface equal to said uniform thickness to allow single blanks to be conveyed past said front brackets by said introductory belts.

17. A method of manufacturing beverage container holders as set forth in claim 16 comprising the additional step of:

providing said front brackets with curved surfaces against which the leading edges of the blanks of said stack of elongated blanks engage as they approach said space between the bottoms of the front brackets and said support surface.

18. A method of manufacturing beverage container holders as set forth in claim 16 comprising the additional step of:

providing vibration producing mechanism including pads that engage the trailing edges of the blanks of said stack of elongated blanks to assist in releasing the blanks from the stack.

19. A method of manufacturing beverage container holders as set forth in claim 10 comprising the additional step of:

applying heat-activated adhesive to a second area of the inner surface of each blank; and crystallizing the heat-activated adhesive that has been applied to the second area of the inner surface of each blank.

20. A method of manufacturing beverage container holders as set forth in claim 19 comprising the additional step of:

providing a source of pressurized air; providing a vortex tube mechanism for each of the areas where the heat-activated adhesive has been applied to the inner surface of each blank; and connecting said source of pressurized air to each of said vortex tube mechanisms to produce streams of freezing air that is used to crystallizing the heat-activated adhesive that has been applied to the areas of the inner surface of each blank.

21. A method of manufacturing beverage container holders as set forth in claim 20 comprising the additional step of:

dividing each stream of freezing air into two different streams; and directing the two different streams of freezing air on the heat activated adhesive that has been applied to the areas of the inner surface of 28 each blank at two separate locations along the path that said conveyor mechanism conveys the blanks.

22. A method of manufacturing beverage container holders as set forth in claim 10 comprising the additional step of:

providing a source of pressurized air;

providing a vortex tube mechanism; and connecting said source of pressurized air to said vortex tube mechanism to produce a stream of freezing air that is used to crystallizing the heat-activated adhesive that has been applied to the area of the inner surface of each blank.

23. A method of manufacturing beverage container holders as set forth in claim 22 comprising the additional step of:

dividing said stream of freezing air into two different streams; and directing the two different streams of freezing air on the heat-activated adhesive that has been applied to the area of the inner surface of each blank at two separate locations along the path that said conveyor mechanism conveys the blanks.

24. A method of manufacturing a disposable beverage container holder, from a pre-manufactured planar paperboard blank, having a frusta-conical shape with an outer linerboard surface and an inner fluted surface comprising the steps of:

providing a stack of pre-manufactured blanks of a uniform thickness, each blank having a central section and two end flaps;

providing an elongated machine having multiple work stations along both sides of its longitudinal extent;

providing a conveyor mechanism that is adapted to engages the central section of said blanks with the end flaps extending there from in cantilever fashion;

releasing blanks from the stack, sequentially in an orientation with the outer surface down and the inner fluted surface up, into said conveyor mechanism;

conveying the blanks at a constant rate along the longitudinal extent of the machine;

skiving the outer linerboard surface of an end flap of each released blank;

folding up the end flap that has been skived such that it lies flat over the central section of the blank;

applying adhesive to the skived area of the flap that is laying flat over the central section of the blank;

folding up the other end flap of the blank such that it overlies the skived area to which adhesive has been applied;

providing a pressure applicator mechanism that will convey the folded blank at a rate that is slower than said constant rate and will apply a downward pressure to the folded blank;

feeding the folded blanks to said pressure applicator mechanism;

feeding the folded blanks at a slower rate than said constant rate;

applying downward pressure to the free end flap that overlies the skived area to which adhesive has been applied;

discharging the finished products in an imbricated arrangement;

picking up groups of finished products from the imbricated arrangement;

compressing the group of finished products in the imbricated arrangement into a stack of printed products; and placing the stack of finished products in a shipping container.

25. A method of manufacturing beverage container holders as set forth in claim 24 comprising the additional step of:

providing a containment apparatus for receiving the stack of pre-manufactured blanks; and providing said containment apparatus with side bars and a back brace to assure proper alignment of the blanks when they are released into the conveyor mechanism.

26. A method of manufacturing beverage container holders as set forth in claim 24 comprising the additional step of:

providing a containment apparatus for receiving the stack of pre manufactured blanks; and providing said containment apparatus with front brackets, side bars and a back brace to assure proper alignment of the blanks when they are released into the conveyor mechanism.

27. A method of manufacturing beverage container holders as set forth in claim 24 comprising the additional step of:

providing a containment apparatus for receiving the stacks of pre manufactured blanks; and providing a set of introductory belts that underlies said containment apparatus and provides a support surface for said stack of pre-manufactured blanks.

28. A method of manufacturing beverage container holders as set forth in claim 27 comprising the additional step of:

providing said containment apparatus with side bars and a back brace to assure proper alignment of the blanks when they are released into the conveyor mechanism.

29. A method of manufacturing beverage container holders as set forth in claim 27 comprising the additional step of:

providing said containment apparatus with front brackets, side bars and a back brace to assure proper alignment of the blanks when they are released into the conveyor mechanism.

30. A method of manufacturing beverage container holders as set forth in claim 29 comprising the additional step of:

supporting said front brackets such that there is space between the bottoms of the front brackets and said support surface equal to said uniform thickness to allow single blanks to be conveyed past said front brackets by said introductory belts.

31. A method of manufacturing beverage container holders as set forth in claim 30 comprising the additional step of:

providing said front brackets with curved surfaces against which the leading edges of the blanks of said stack of pre-manufactured blanks engage as they approach said space between the bottoms of the front brackets and said support surface.

32. A method of manufacturing beverage container holders as set forth in claim 30 comprising the additional step of:

providing vibration producing mechanism including pads that engage the trailing edges of the blanks of said stack of pre-manufactured blanks to assist in releasing the blanks from the stack.

33. A method of manufacturing beverage container holders as set forth in claim 24 comprising the additional steps of:

applying heat-activated adhesive to an area of the inner fluted surface of each blank; and crystallizing the heat-activated adhesive that has been applied to the area of the inner fluted surface of each blank.

34. A method of manufacturing beverage container holders as set forth in claim 33 comprising the additional step of:

providing a containment apparatus for receiving the stack of pre manufactured blanks; and providing said containment apparatus with side bars and a back brace to assure proper alignment of the blanks when they are released into the conveyor mechanism.

35. A method of manufacturing beverage container holders as set forth in claim 33 comprising the additional step of:

providing a containment apparatus for receiving the stack of pre manufactured blanks; and providing said containment apparatus with front brackets, side bars and a back brace to assure proper alignment of the blanks when they are released into the conveyor mechanism.

36. A method of manufacturing beverage container holders as set forth in claim 33 comprising the additional step of:

providing a containment apparatus for receiving the stacks of pre-manufactured blanks; and providing a set of introductory belts that underlies said containment apparatus and provides a support surface for said stack of pre-manufactured blanks.

37. A method of manufacturing beverage container holders as set forth in claim 36 comprising the additional step of:

providing said containment apparatus with side bars and a back brace to assure proper alignment of the blanks when they are released into the conveyor mechanism.

38. A method of manufacturing beverage container holders as set forth in claim 36 comprising the additional step of:

providing said containment apparatus with front brackets, side bars and a back brace to assure proper alignment of the blanks when they are released into the conveyor mechanism.

39. A method of manufacturing beverage container holders as set forth in claim 38 comprising the additional step of:

supporting said front brackets such that there is space between the bottoms of the front brackets and said support surface equal to said uniform thickness to allow single blanks to be conveyed past said front brackets by said introductory belts.

40. A method of manufacturing beverage container holders as set forth in claim 39 comprising the additional step of:

providing said front brackets with curved surfaces against which the leading edges of the blanks of said stack of pre-manufactured blanks engage as they approach said space between the bottoms of the front brackets and said support surface.

41. A method of manufacturing beverage container holders as set forth in claim 39 comprising the additional step of:

providing vibration producing mechanism including pads that engage the trailing edges of the blanks of said stack of pre-manufactured blanks to assist in releasing the blanks from the stack.

42. A method of manufacturing beverage container holders as set forth in claim 33 comprising the additional step of:

applying heat-activated adhesive to a second area of the inner fluted surface of each blank; and crystallizing the heat-activated adhesive that has been applied to the second area of the inner fluted surface of each blank.

43. A method of manufacturing beverage container holders as set forth in claim 42 comprising the additional step of:

providing a source of pressurized air;

providing a vortex tube mechanism for each of the areas where the heat-activated adhesive has been applied to the inner fluted surface of each blank; and connecting said source of pressurized air to each of said vortex tube mechanisms to produce streams of freezing air that is used to crystallizing the heat-activated adhesive that has been applied to the areas of the inner fluted surface of each blank.

44. A method of manufacturing beverage container holders as set forth in claim 43 comprising the additional step of:

dividing each stream of freezing air into two different streams; and direction the two different streams of freezing air on the heat activated adhesive that has been applied to the areas of the inner fluted surface of each blank at two separate locations along the path that said conveyor mechanism conveys the blanks.

45. A method of manufacturing beverage container holders as set forth in claim 33 comprising the additional step of:

providing a source of pressurized air; providing a vortex tube mechanism; and connecting said source of pressurized air to said vortex tube mechanism to produce a stream of freezing air that is used to crystallizing the heat-activated adhesive that has been applied to the area of the inner fluted surface of each blank.

46. A method of manufacturing beverage container holders as set forth in claim 45 comprising the additional step of:

dividing said stream of freezing air into two different streams; and directing the two different streams of freezing air on the heat activated adhesive that has been applied to the area of the inner fluted surface of each blank at two separate locations along the path that said conveyor mechanism conveys the blanks.

* * * * *